United States Patent [19]

Ahern et al.

[11] Patent Number: 4,743,453

[45] Date of Patent: * May 10, 1988

[54] FERMENTATION OF WHEY TO PRODUCE PROPIONIC ACID

[75] Inventors: William P. Ahern; Dale F. Andrist; Lawrence E. Skogerson, all of Rochester, Minn.

[73] Assignee: Stauffer Chemical Co., Westport, Conn.

[*] Notice: The portion of the term of this patent subsequent to Jun. 30, 2004 has been disclaimed.

[21] Appl. No.: 671,140

[22] Filed: Nov. 13, 1984

[51] Int. Cl.$^4$ .................. A23C 29/02; C12P 39/00; C12P 7/52; C12R 1/01
[52] U.S. Cl. ........................ 426/41; 426/43; 435/42; 435/141; 435/822
[58] Field of Search ............. 435/41, 42, 141, 822; 426/41, 42, 43

[56] References Cited

U.S. PATENT DOCUMENTS

| | | | |
|---|---|---|---|
| 1,865,146 | 6/1932 | Sherman | 435/141 |
| 1,875,401 | 9/1932 | Woodruff et al. | 435/42 |
| 1,946,447 | 2/1934 | Stiles | 435/822 |
| 2,465,905 | 3/1949 | Meade et al. | 426/41 |
| 3,852,158 | 12/1974 | Anderson et al. | 426/41 |
| 4,020,185 | 4/1977 | Andersen et al. | 426/43 |
| 4,497,833 | 2/1985 | Anderson | 426/41 |

FOREIGN PATENT DOCUMENTS 2438429 6/1980 France ................... 426/42

*Primary Examiner*—David M. Naff
*Assistant Examiner*—William J. Herald
*Attorney, Agent, or Firm*—Michael J. Bradley

[57] ABSTRACT

A process for manufacture of fermented whey having a high concentration of divalent ion propionate is disclosed in which a whey medium having a solids content ranging from about 0.5% to about 18% by weight is prefermented with a galactose and glucose utilizing lactic acid producing organism, neutralized with a divalent metallic ion hydroxide and sterilized. The sterilized medium is then inoculated with a propionic acid-producing bacterium and incubated for a sufficient period of time to produce a high concentration of divalent metallic ion propionate. The divalent metallic ion is preferably calcium, and the whey medium preferably contains yeast extract.

8 Claims, No Drawings

FERMENTATION OF WHEY TO PRODUCE PROPIONIC ACID

BACKGROUND OF THE INVENTION

Whey, a naturally occuring substance, is the serum or watery part of milk which is separated from the curds in the process of making cheese. Dried whey is comprised of about 13% protein and 73% lactose, and the balance inorganic salts. One of the uses of whey in commerce is to ferment it and incorporate it into bakery products, where it acts as a mycostatic agent, thus enabling the products to have substantially longer shelf lives than would otherwise be possible. It has been determined that the active mycostatic agent in whey is propionic acid which is produced as a consequence of the fermentation process.

Suggested bacteria for fermentation, as disclosed in U.S. Pat. No. 1,910,130, include Bacterium acidi-propionici. In previously described processes producing fermented whey, it was desirable to sterilize the whey and to ferment it with a known non-pathogenic culture in order to keep out pathogens, and control the product quality and specifications. One of the steps in the process of fermentation is the sterilization of the whey substrate, which must be done without adversely effecting the subsequent fermentation. Sterilization is necessary in order to kill any residual organisms in the whey prior to introducing the organism for fermentation.

Further, to produce the desired calcium propionate or other divalent metallic ion ($M^{++}$) propionate product a difficult to handle and sterilize $Ca(OH)_2$/NaOH or $M(OH)_2$/NaOH slurry system was needed for pH control. Therefore, sterile NaOH was used for pH control producing the less desirable sodium propionate. In the improved two-stage sequential fermentation described herein, calcium or other divalent metallic ion is introduced by pre fermenting pasteurized whey with a galactose and glucose utilizing lactic acid-producing bacterial culture or mixture of bacterial cultures and controlling the pH with $Ca(OH)_2$ or $M(OH)_2$. This fermented whey, containing high concentrations of Ca-lactate or M-lactate and no residual reducing sugars, is then sterilized and fermented with a pure culture of propionic acid-producing bacterium to produce high concentrations of calcium propionate or other divalent metallic ion propionates.

DESCRIPTION OF THE INVENTION

To introduce calcium propionate or other divalent metallic ion propionate into a functionalized whey product, pasteurized whey is fermented with a galactose and glucose utilizing lactic acid-producing bacterial culture or mixture or lactic acid-producing bacterial cultures, i.e., *Lactobacillus acidophilus* and *Streptococcus thermophilus*. As the fermentation continues the lactose is converted to lactic acid. The pH is controlled at about 5.5–6.0 by adding $Ca(OH)_2$ or $M(OH)_2$ or mixtures thereof. After about 18 hours the fermentation is completed. The resulting broth is adjusted to pH 7 with $Ca(OH)_2$ or $M(OH)_2$ or mixtures thereof, sterilized by UHT, and fermented with a pure culture of propionic acid-producing bacterial cultures. The pH of the pure culture fermentation is controlled with NaOH. The lactic acid and any remaining reducing sugar is converted to calcium propionate. By using this sequential twostep fermentation, a product containing 85% or more calcium propionate or other divalent metallic ion propionate is obtained.

Lactic acid-producing bacterial fermentation of a pasteurized whey broth comprising unhydrolyzed whey (acid or sweet) and yeast extract results in lactic acid formation. This anaerobic fermentation can be carried out preferably in a pH range of 4.0 to 8.5, preferably with the pH maintained in a range from about 4.5 to about 6.0. The fermentation can be carried out at a temperature from about 35° to 60° C., preferably carried out at a temperature from about 40° to about 50° C. Typical composition of Teklac (sweet dairy whey) is as follows:

| CHEMICAL AND PHYSICAL SPECIFICATIONS | | |
|---|---|---|
| Ingredient Listing: Whey | | |
| Typical Proximate Analysis | | |
| Protein (N × 6.38)% | 12.7 | |
| Fat % | 1.1 | (1.25% Maximum) |
| Moisture % | 4.5 | (5.0% Maximum) |
| Ash % | 8.0 | |
| Lactose % | 71.3 | |
| Calories, Cal/100 g | 350.0 | |
| Typical Vitamin & Mineral Analysis | | |
| Vitamin A I.U./100 g | Nil | |
| Vitamin C mg/100 g | Nil | |
| Thiamin mg/100 g | 0.40 | |
| Riboflavin mg/100 g | 1.76 | |
| Niacin mg/100 g | 1.00 | |
| Calcium % | 0.71 | |
| Iron % | Nil | |
| Vitamin $B_{12}$ ug/100 g | 2.12 | |
| Phosphorous % | 0.69 | |
| Pantothenic Acid mg/100 g | 4.09 | |
| Microbiological Standards | | |
| Standard Plate Count | 10,000/g | (Maximum) |
| Coliforms | 9/g | (Maximum) |
| *E. coli* | Negative | |
| Salmonella | Negative | |

The nutritional values listed above are within 80% of the value declared in compliance with Federal Nutritional Regulations 21 CFR §1.17(4)(ii).

| | Typical Range | Limit |
|---|---|---|
| Solubility Index | 0.1–0.5 ml | 1.25 ml Max. |
| Acidity | 0.10–0.14% | 0.16 Max. |
| Alkalinity of Ash | 175–200 ml | 225 ml Max. |
| Scorched Particles | 7.5 mg | 15.0 mg Max. |
| Particle size (Through 40 Mesh) | 99–100% | 98% Min. |

Concentration of whey solids can range from 0.5% to about 18.0%, preferably from about 6% to about 12%, and the concentration of added yeast extract in the fermentation broth can range from about 0.5% to about 4.0%, preferably from about 0.3% to about 2.0%. Sufficient yeast extract to supplement both fermentations is added before the first fermentation for convenience only. The yeast extract may be added before each fermentation if desired. Lactic acid concentrations of about 5.0% are usually reached within 18 hours using 8% whey solids. All of the above weight percents are in weight per volume.

The pasteurized, fermented whey described above is neutralized with $Ca(OH)_2$ or $M(OH)_2$ or mixtures thereof to a pH of 6.0 to 7.0, UHT sterilized, and fermented with a propionic acid-producing bacterium. The preferred divalent metallic ion hydroxide is selected from the group consisting of calcium hydroxide, magnesium hydroxide, barium hydroxide, manganese hydroxide and mixtures thereof. Calcium hydroxide is the most preferred divalent metallic ion hydroxide. This anaerobic fermentation can be carried out preferably in a pH range of 5.5 to 8.5 Preferably with the pH maintained in a range from about 6.0 to about 7.0. The fermentation can be carried out at a temperature from about 20° to 40° C., preferably carried out at a temperature from about 35° to 40° C. Propionic acid concentrations of about 2.6% are usually reached within 60 hours at 12% solids fed to the prepfermentation zone.

MICROORGANISMS

Preferred lactic acid-producing bacteria for use as a starter culture in the pre-fermentation process are strains of:
 (a) *Streptococcus thermophilus;*
 (b) *Lactobacillus acidophilus;*
 (c) *Lactobacillus bulgaricus;* and
 (d) mixtures of the above organisms,
that have been selected for their ability to utilize galactose and glucose.

Preferred propionic acid-producing bacteria for use in the second fermentation process are:
 (a) *Propionibacterium freudenreichii* ss. *shermanii*
 (b) *Propionibacterium acidi-propionici*

ULTRA HIGH TEMPERATURE (UHT) STERILIZATION

An ultra high temperuture (UHT) sterilization method is a method of sterilization of whey by direct steam injection that results in a whey medium temperature of at least 140° C. held for from about 4 to about 20 seconds. Several types of equipment are available to achieve UHT, such as an α-Laval sterilizaer made by α-Laval or an APV heat exchanger made by APV Company, Inc., Tonawanda, N.Y.

CULTURE STORAGE AND PREPARATION OF INOCULUM LACTIC ACID-PRODUCING BACTERIA

*Streptococcus thermophilus, Lactobacillus acidophilus* and *Lactobacillus bulgaricus* were stored in MRS (Difco) agar slants. Slants were incubated at 43° C. for 18–24 hours, and stored at 4° C. for up to 6 months. A slant was revived by overlaying with 5 ml of MRS broth and incubating for 24 hours at 43° C. The revived slant was transferred to a 1000 ml Erlenmeyer flask containing 500 ml of sterile medium. The medium contained 2% spray dried sweet whey and 1% yeast extract. The flasks were incubated for 18–24 hours and stored at 4° C. These flasks are used to inoculate the laboratory fermentors.

Propionic Acid-Producing Bacteria

*P. shermanii* was stored in sodium lactate stabs (10 g trypticase, 10 g yeast extract, 10 g Na Lactate, 0.25 g $K_2HPO_4$, 12 g Agar, one l deionized water, 50 ml/25 mm × 150 mm screw-capped tube). Stabs were inoculated, incubated at 30° C. for 72 hours and stored at 4° C. for up to 6 months. A stab was revived by overlaying with 10 ml Hansen's glucose broth (HGB) (20 g trypticase, 5 g yeast extract, 5 g glucose, one l deionized water) and incubating for 48 hours at 30° C.

A shake flask containing 2% Teklac medium was inoculated with 10 ml HGB from one revived stab (*P. shermanii*). The flasks were incubated for 48 hours. These cultures were then used to inoculate production fermentors.

MEDIUM FOR PREPARATION OF LACTIC ACID-PRODUCING BACTERIA AND OPERATION OF THE 14 LITER LABORATORY FERMENTOR

Fresh pasteurized whey at approximately 6.5% total solids (T.S.) was the medium used for the inoculum build-up. Prior to use the microfirm glass jar fermentor (New Brunswick Scientific, Edison, N.J.) was sterilized by autoclaving at 250° F. for 30 minutes. Twelve liters of pasteurized whey was inoculated with lactic acid-producing organisms. The fermentor was operated at 43° C., no gas was sparged, agitation was 120–160 rpm, and pH was maintained at 6.5 with concentrated NaOH (25%).

MEDIUM FOR THE PREPARTAION OF LABORATORY INOCULUM IN 6 LITER SHAKE FLASKS

The whey medium contained 2% dried sweet whey, 1% yeast extract, 0.03% thioglycolic acid, and 0.25% calcium carbonate. Four liters of medium were added to each shake flask along with three drops of FG-10 antifoam (Dow Chemical Corp.). Flasks were autoclaved in a steam sterilizer at 250° F. for 50 minutes. Inoculated flasks were incubated in a G-25 shaker/incubator (New Brunswick Scientific, Edison, N.J.) at 30° C. for 48 hours.

ASSAYS

Lactic acid and lactose were estimated by utilizing a Waters high pressure liquid chromatography unit (Waters Instruments, New Milford, Mass.). Propionic acid (HPr) and acetic acid (HAc) were assayed by gas chromatography. A Packard Model 5880A with a capillary column (J & W DX4 column) and a flame ionization detector were used. The column temperature was programmed to begin at 90° C. and increase to 250° C. at a rate of 10°/min., injector and detector temperatures were 275° C. The carrier gas was helium with a flow rate of 1.5 ml per minute. Samples were prepared by adding 5 ml of broth to 45 ml of 2% $H_3PO_4$ containing a valeric acid internal standard. Cells and other suspended solids were removed by filtering through a 0.45 micron acrodisc (Gillman Scientific). One microliter of the acidified filtrate was injected using a 1.0 ul Hamilton N701 syringe. Results were calculated from a standard curve.

EXAMPLE I

Batch fermentations of directly UHT sterilized whey medium containing 12% whey plus 1% yeast extract using pure culture *P. shermanii* resulted in 1.6–2.2% propionic acid produced within 70 hours. More than 50% of the lactose was not used. Table I shows the results of a typical reaction.

TABLE I

| Time (hr.) | Lactose | Propionic Acid | Acetic Acid |
|---|---|---|---|
| 0 | 6.5 | — | — |
| 23 | 5.4 | 0.5 | 0.2 |
| 48 | 5.2 | 1.2 | 0.3 |
| 66 | 3.8 | 1.6 | 0.4 |

EXAMPLE II

Fresh whey (10% solids) was received and pasteurized without pH adjustment. Fermentation was initiated by the addition of galactose and glucose utilizing strains of *Lactobacillus acidophilus* and *Streptococcus thermophilus*.

When the pH had decreased to about 4.3, sufficient lime slurry was added to neutralize the lactic acid and bring the pH up to about 6. This procedure was repeated until the pH no longer decreased. At this point there were no detectable reducing sugars remaining.

The pH was adjusted to 7 with lime and the media was sterilized by UHT and inoculated with *P. shermanii*. Caustic was added on demand for 24 hours to maintain pH of 7. The addition rate was then decreased so that the final broth was pH of 6. The results are shown in Table II. After 56 hours the propionic acid concentration was 2.5 weight percent.

TABLE II

*P. Shermanii* Fermentation of Pre-Fermented Whey Medium pH controlled with Sterile NaOH Between 6 and 7

| | Weight Percent in Broth | | | | |
|---|---|---|---|---|---|
| Time (hr.) | Lactose | Galactose | Lactic Acid | Propionic Acid | Acetic Acid |
| 0 | N.D. | 0.1 | 5.3 | — | — |
| 8 | 0.1 | N.D. | 3.6 | 0.7 | 0.5 |
| 16 | 0.1 | 0.1 | 3.2 | 1.0 | 0.2 |
| 24 | N.D. | 0.1 | 2.4 | 1.4 | 0.8 |
| 32 | 0.1 | 0.1 | 1.8 | 1.7 | 0.9 |
| 40 | 0.1 | N.D. | 1.0 | 2.1 | 1.1 |
| 48 | 0.2 | 0.1 | 0.6 | 2.3 | 1.1 |
| 56 | 0.1 | 0.1 | 0.4 | 2.5 | 1.2 |

N.D. = Not detectable.

What is claimed is:

1. In a process for functionalizing whey containing from about 0.5% to about 18% by weight whey solids by sterilizing the whey and then fermenting the whey with a propionic acid-producing organism to produce propionic acid, the improvement comprising:
   (a) forming a pre-fermentation broth of whey containing from about 0.5% to about 18% by weight whey solids and yeast extract; and
   (b) fermenting the pre-fermentation broth with a galactose and glucose utilizing lactic acid-producing organism or mixture of galactose and glucose utilizing lactic acid-producing organisms to ferment the lactose in the whey to lactic acid;
   (c) neutralizing the fermented lactic acid containing pre-fermentaiton broth with a divalent metallic ion hydroxide; and
   (d) sterilizing the neutralized, fermented lactic acid containing pre-fermentation broth and fermenting the broth with a propionic acid-producing organism to produce propionic acid.

2. The process of claim 1 wherein the divalent metallic ion hydroxide is selected from the group consisting of calcium hydroxide, magnesium hydroxide, barium hydroxide, manganese hydroxide and mixtures thereof.

3. The process of claim 1 wherein the sterilization step is conducted by direct steam injection that results in a whey medium temperature of at least 140° C. held for from about 4 to about 20 seconds.

4. The process of claim 3 wherein the divalent metallic ion hydroxide is selected from the group consisting of calcium hydroxide, magnesium hydroxide, barium hydroxide, manganese hydroxide and mixtures thereof.

5. The process of claim 1 wherein the lactic acid-producing organism is selected from the group consisting of *Streptococcus thermophilus*, *Lactobacillus acidophilus*, *Lactobacillus bulgaricus* and mixtures thereof and the propionic acid-producing organism is selected from the group consisting of *Propionibacterium freudenreichii* ss. *shermanii* and *Propionibacterium acidi-propionici*.

6. The process of claim 4 wherein the lactic acid-producing organism is a mixture of *Lactobacillus acidophilus* and *Streptococcus thermophilius* and the propionic acid-producing organism is *Propionibacterium freudenreichii* ss. *shermanii*.

7. The process of claim 6 wherein the concentration of yeast extract is from about 0.3 to about 2.0% by weight.

8. The process of claim 7 wherein the concentration of the whey solids is from about 6.0 to about 12.0% by weight.

* * * * *